United States Patent
Olek et al.

(10) Patent No.: US 6,214,556 B1
(45) Date of Patent: Apr. 10, 2001

(54) METHOD FOR PRODUCING COMPLEX DNA METHYLATION FINGERPRINTS

(75) Inventors: Alexander Olek, Berlin; Sven Stefan Olek, Heidelberg; Jörn Walter, Berlin, all of (DE)

(73) Assignee: Epigenomics AG (DE)

( * ) Notice: Subject to any disclaimer, the term of this patent is extended or adjusted under 35 U.S.C. 154(b) by 0 days.

(21) Appl. No.: 09/381,610

(22) PCT Filed: Nov. 27, 1998

(86) PCT No.: PCT/DE98/03558

§ 371 Date: Sep. 22, 1999

§ 102(e) Date: Sep. 22, 1999

(87) PCT Pub. No.: WO99/28498

PCT Pub. Date: Jun. 10, 1999

(30) Foreign Application Priority Data

Nov. 27, 1997 (DE) .............................................. 197 54 482

(51) Int. Cl.⁷ .............................. C12Q 1/68; C12P 19/34; C07H 19/00

(52) U.S. Cl. ........................... 435/6; 435/91.2; 536/22.1; 536/23.1; 536/24.31

(58) Field of Search .................. 435/6, 91.2; 536/24.31, 536/24.33, 22.1, 23.1

(56) References Cited

PUBLICATIONS

Xiong, Z et al, "COBRA: a sensitive and quantitative DNA methylation assay", Nucleic Acids Research, 1997, vol. 25, No. 12, pp. 2532–2534.*

\* cited by examiner

*Primary Examiner*—John S. Brusca
*Assistant Examiner*—Stephen Siu
(74) *Attorney, Agent, or Firm*—Kriegsman & Kriegsman

(57) ABSTRACT

Method for characterizing, classifying and differentiating tissues and cell types, for predicting the behavior of tissues and groups of cells, and for identifying genes with changed expression. The method involves obtaining genomic DNA from a tissue sample, the genomic DNA subsequently being subjected to shearing, cleaved by means of a restriction endonuclease or not treated by either one of these methods. The base cytosine, but not 5-methylcytosine, from the thus-obtained genomic DNA is then converted into uracil by treatment with a bisulfite solution. Fractions of the thus-treated genomic DNA are then amplified using either very short or degenerated oligonucleotides or oligonuclcotides which are complementary to adaptor oligonucleotides that have been ligated to the ends of the cleaved DNA. The quantity of the remaining cytosines on the guanine-rich DNA strand and/or the quantity of guanines on the cytosine-rich DNA strand from the amplified fractions are then detected by hybridization or polymerase reaction, which quantities are such that the data generated thereby and automatically applied to a processing algorithm allow the drawing of conclusions concerning the phenotype of the sample material.

24 Claims, No Drawings

METHOD FOR PRODUCING COMPLEX DNA METHYLATION FINGERPRINTS

1. AREA OF THE INVENTION

The method to be patented here provides a new possibility for the differential diagnosis of cancer diseases. It leads to a deeper understanding of carcinogenesis and of the pathogenesis of polygenic inherited diseases. The method furthermore concerns the identification of all the genes participating in the development of diseases. As in the past, cell differentiation and the differentiation of higher organisms remains essentially not understood. Here too, the method promises to considerably increase knowledge.

The levels of observation that have been well studied by the methodological developments of recent years in molecular biology include the gene itself, the translation of genes in RNA, and the resulting proteins. When, during the course of the development of an individual, a gene is switched on, and how the activation and inhibition of certain genes in certain cells and tissues is controlled, can be correlated with a high degree of probability with the extent and the character of the methylation of the gene or the genome. In this regard, it is reasonable to assume that pathogenic conditions are expressed in a modified methylation pattern of individual genes or of the genome.

The state of the art is a method which allows the study of the methylation pattern of individual genes. More recent additional developments of this method also allow the analysis of minute quantities of starting material, where, however, the total number of measurement points remains at most a two-digit number, in theoretical range of values of at least $10^7$ measurement points. Using the method to be patented, it is now possible, for the first time, to examine any desired sections of the genome with any desired number of measurement points. Thus, the method allows the identification of causes for genetic diseases of all types that could not be determined by any other means, and it allows the development of new treatment strategies and the identification of target proteins for new drugs.

2. STATE OF THE ART 2.1 State of the Art of Molecular Analysis of Cell Phenotypes The study of gene expression can be at the RNA level or at the protein level. Both levels in principle reflect important phenotypic parameters. Protein assays using two-dimensional gels (McFarrel method) have been known for approximately 15 years. Using these assays, it is possible to elaborate the analysis of the chromatographic positions of several thousand proteins. Very early on, such electropherograms were already processed or evaluated with data processing means. In principle, the validity of the method is high, however, it is inferior to the modern methods of gene expression based on RNA analysis in two regards.

In particular, the detection of proteins that are of regulatory importance, from small quantities of cells, fails because of the fact that the sensitivity of the methods used is much too low. Indeed, in contrast to nucleic acids, proteins cannot be amplified. In addition, the method is very complex, not amenable to automation, and very expensive. In contrast, RNA analysis presents considerable advantages, and due to of the use of PCR it is more sensitive. Above all, each RNA species recognized to be important can be identified immediately by its sequence.

Overexpression or underexpression of individual RNAs with a known sequence can usually be easily detected; however, in connection with the applications discussed here, they are only valid in exceptional cases.

The method of "differential displays" at best allows a semiquantitative study of expression. Expression products amplified by PCR are separated by gel electrophoresis. The validity is limited as a result of the resolution of the gel electrophoresis. In addition, the method is insufficiently sensitive and robust for use in routine diagnosis (Liang, P. and Pardee, A. B., Science 257, 967–971).

Genes with high overexpression or underexpression are frequently identified by subtractive techniques. Here, cDNA clones of a cell or tissue species to be examined are plated. Against the clones, CDNA is hybridized as comparison material. Expression patterns cannot be reliably prepared using this technique.

One activity of the American "human genome project" is the systematic sequencing of expressed genes. The data obtained from this can be used to build expression chips, which allow the study of practically all expressed sequences of a cell or tissue type in a single experiment.

2.2 State of the Art in the Analysis of Cancer Diseases

Mutations in genes always trigger cancer diseases [sic], that is, cell degeneration. The causes of these mutations can be exogenous influences, or events in the cell. In a few exceptional cases, an individual mutation, which frequently affects larger regions of the genome (translocations, deletions), results in the degeneration of the cell; but in most cases a chain of mutations on different genes is involved, and it is only their combined effect that results in the malignant disease. These results on the DNA level are also reflected on the RNA and protein levels. In this context, it is highly probable that a multiplication occurs, because it is certain that in many cases the quantity and type of one RNA influences the extent of the synthesis of several other RNA species. This leads to a change in the synthesis rates of the corresponding proteins, which, in turn, can result in deregulating metabolism, and thus initiate the mechanism of regulation and counter regulation. The result is a gene expression pattern of the cells in question, that has been modified in a very specific (but largely nondeterminable) manner▶ the specificity is for a certain carcinoma, for the stage of the carcinoma, and the degree of malignancy of the carcinoma. So far, such phenomena have been outside the realm of study of natural sciences. Indeed, it has been impossible to examine the gene expression or the metabolism of a cell in its totality. Chip technology for the first time provided such a possibility (Schena, M. et al., Science 270, 467–470).

If one wishes to solve the diagnostic problem of early diagnosis of tumors on the molecular level, then one is confronted, today, with an insurmountable difficulty, with very few exceptions: Because, for most tumors, the knowledge of the molecular events, that is, the different mutations, is only fragmentary; researchers do not know what to look for in medical examination material. This means it is absolutely impossible to apply the remarkable sensitivity and specificity of the polymerase chain reaction. Examples are certain intestinal tumors, Ewing's sarcoma, and certain forms of leukemia, which are in fact each defined by a single, precisely described mutation. In those cases, it is possible to identify the degenerated cell among millions of normal cells. However, even within these apparently unambiguously defined tumor groups, there are such differences in the behavior that the conclusion must be drawn that additional unknown genetic parameters (such as, for example, the genetic background of the individual) play an important role. Immunological tumor markers are helpful auxiliary parameters, but they continue to make only a modest contribution, in addition to the other conventional diagnostic parameters. However, they can be used for the purpose of preselecting suspect cells.

Histology plays an important and indispensable role in the identification of degenerated tissues, but not precisely in early diagnosis.

Thus, because most tumors are not sufficiently characterized for diagnostic purposes on the molecular level, as a rule, no possibilities exist to proceed to a subdivision into stages or even a subdivision by degrees of risk. Such a subdivision, however, is an absolute prerequisite for an improved selection of treatments and, above all, for the development of effective new drugs and of gene therapy.

2.3 State of the Art in Research on the Number, Type and Properties of the Possible Stable States of Cells of Higher Organisms In recent times, there has been an increase in the number of indications that complex regulatory systems (an excellent example of which is cell regulation), when left alone, can exist in only a limited number of stable states, above a critical minimum complexity and below a critical maximum connectivity (of the average number of the components, with which any given component is connected) (Kauffman, S. A., Origins of Order, Oxford University Press, 1993). In this context, the word state should be understood as the concept of selection for the general phenomenon. In connection with cells as biological regulatory systems, one can also talk of differentiation state or cell type. Although no such connection has been demonstrated—and even a mere limitation of the possible states for biological systems has not been demonstrated—the practical implications would be of very great importance: If, regarding the constant information content of the cells of an organism (de facto, such constancy essentially exists within one species), there were only a limited number of stable states, then it would be likely that degenerated cells could also be in only one of these states or in a transition between the possible states. At this time, there is no possibility to define these states on a molecular basis. It is hardly possible to achieve a correlation between the individual states and the behavior of the cells according to the state of the art. However, such an analysis could make decisive contributions to the diagnosis and prognosis of diseases. It is even possible that a correlation could be established between the possible states of diseased cells and the best suited therapy. Furthermore, it is probable that such a method could also have a decisive influence in the selection of the time of treatment. For example, if one were to discover that the cells of a tumor are in a transition between possible states, one could assume that such a population of cells would be more likely to yield to the selection pressure resulting from the treatment, and thus could escape more easily. A cell population in such a scenario, within such transitional states, would have a considerably increased flexibility, and it would be easily forced into a possible stable state, in which the selection pressure would be eliminated, and the treatment would thus be without effect. A method which could classify cells and cell groups according to states would then also contribute to recognizing, understanding and possibly solving such problems. However, according to the state of the art, it is not possible to determine whether only a limited number of states of cells exists. It follows that it is not possible to differentiate groups of cells according to an abstract criterion concerning their states, and to predict these states with a certain behavior of the cells.

2.4 Hereditary Diseases

Today, the genetic map of the human genome comprises 2500 so-called microsatellites. These instruments are used to locate a multitude of genes, usually genes whose defect causes a genetic disease, per linkage analysis, and then to identify them. Common genetic diseases caused by a single defective gene are thus elucidated, from the point of view of the geneticist's principle, polygenic diseases should also be understood in this manner. Many polygenic diseases are very common, so common that they are included among the so-called wide-spread diseases. Asthma and diabetes are examples. Many carcinoma types are also included. The use of the above-described strategy of linkage analysis also produced enormous initial successes. In many instances, numerous causal genes of important polygenic diseases such as diabetes, schizophrenia, atherosclerosis and obesity have been found. Besides the availability of the molecular biology laboratory techniques proper, the availability of a relatively large number of patients and relatives affected by each disease is a crucial prerequisite for genetic elucidation. In the past two years it has become apparent that the number of several hundred patients that were originally used for the linkage analysis of polygenic diseases very likely is too low by one order of magnitude. This applies, in any case, to cases where the entire spectrum of the causal gene is to be elucidated. Because the level of manual work required for such a linkage analysis is extraordinarily high, only very slow progress can be expected in the analysis of polygenic diseases. Alternative strategies are sought because it is precisely these diseases that are of enormous social and economic importance.

2.5 State of the Art DNA Chips

The principle of Affimetrix has progressed the furthest of all the developments (for example, U.S. Pat. Nos. 5,593,839, 5,999,695 or 5,631,734). However, a number of other companies and research projects have produced DNA chips with various properties for special applications (for example, U.S. Pat. Nos. 5,667,667, 5,525,464 or 5,492,806 or, for example, Goffeau, A., Nature 385, 202–203; Weiler, J. and Hoheisel, J., Anal. Biochem. 243, 218–227; Chee, M. et al., Science 274, 610–614). The most recent publications already report on a commercially available HIV chip, which allows the examination of the complete HIV genome. Fluorescence-labeled PCR products of the sample to be examined are hybridized with up to 400,000 oligonucleotides. The evaluation of the signals is carried out with the help of CCD cameras. The known capacity of such systems for allele-specific hybridization has been used for a long time. This means that only in places where the sample is absolutely complementary to a fixed oligonucleotide will the signal be maintained at the end of the hybridization and washing procedures. The examination of a known gene sequence to detect mutations succeeds because every partial region of the entire sequence is present in the form of oligonucleotide sequences on the matrix, and the same can be said of every possible deviation from the normal sequence. The efficiency of the chip procedure is due, in part, to the fact that the sequence information for a large number of genes or gene loci is obtained by two simple work steps, namely hybridization and washing.

2.6 Analysis Methods for Measurement of Length

Several embodiment variants of the method according to the invention require, at the end of the procedure, an extremely rapid and precise weight determination. Since a measurement of fragment lengths must be performed for tens of thousands of data points, an extremely efficient measuring system is required. According to the state of the art, possible systems include automatic sequencing apparatuses (U.S. Pat. No. 4,811,218), capillary electrophoresis (for example, Woolley, A. T., et al., Anal. Chem. 68, 4081–4086), MALDI-TOF (Siegert, C. W., et al., Anal. Biochem. 253, 55–65) and separation by chemical labeling (WO 95/04160). The state of the art allows an efficient implementation of these methods, although considerable modifications and incorporation into the novel logics of the method according to the invention are required.

2.6.1 Mass spectrometric methods

The weight of short DNA sequences can be determined with precision in MALDI-TOF mass spectrometers. Furthermore, methods exist in the state of the art which combine these analytical methods with primer extension reactions. In this process, for example, an oligonucleotide with a specific sequence is hybridized with a DNA sample, and only one of the four nucleotides is added per reaction. Knowing which one of the nucleotides has been applied after the hybridization by a polymerase to the 3' end of the oligonucleotide allows the determination of the identity of the base behind the 3' terminus of the oligonucleotide. Variants of this method include one which allows the determination of the length of such repetitive sequences which contain only two of the four possible bases. In this process, the natural nucleotides that are complementary with the occurring bases, and one or both additional so-modified nucleotides are added as terminators of the polymerized reaction, so that the reaction stops after the repeating sequence. Normally the terminators are ddNTPs. From the measurement of the lengths, the length of the repeating sequence can be derived.

2.7 State of the Art Methylation Analysis

The modification of the genomic base cytosine to 5'-methylcytosine represents the epigenetic parameter which to date is the most important one and has been best examined. Nevertheless, methods exist today to determine comprehensive genotypes of cells and individuals, but no comparable methods exist to date to generate and evaluate epigenotypic information on a large scale.

In principle, there are three methods that differ in principle for determining the 5-methyl state of a cytosine in the sequence context.

The first method is based in principle on the use of restriction endonucleases (RE), which are "methylation-sensitive." REs are characterized in that they produce a cut in the DNA at a certain DNA sequence which is usually 4–8 bases long. The position of such cuts can be detected by gel electrophoresis, transfer to a membrane and hybridization. Methylation-sensitive means that certain bases within the recognition sequence must be unmethylated for the step to occur. The band pattern after a restriction cut and gel electrophoresis thus changes depending on the methylation pattern of the DNA. However, most CpG that can be methylated are outside of the recognition sequences of REs, and thus cannot be examined.

The sensitivity of this method is extremely low (Bird. A. P., Southern, E. M., J. Mol. Biol. 118, 27–47). A variant combines PCR with this method; an amplification by two primers located on both sides of the recognition sequence occurs alter a cut only if the recognition sequence is in the methylated form. In this case, the sensitivity theoretically increases to a single molecule of the target sequence; however, only individual positions can be examined, at great cost (Shemer, R. et al., PNAS 93, 6371–6376).

The second variant is based on the partial chemical cleavage of whole DNA, using the model of a Maxam-Gilbert sequencing reaction, ligation of adaptors to the ends thus generated, amplification with generic primers, and separation by gel electrophoresis. Using this method, defined regions having a size of less than thousands of base pairs can be examined. However, the method is so complicated and unreliable that it is practically no longer used (Ward, C, et al., J. Biol. Chem. 265, 3030–3033).

A new method for the examination of DNA to determine the presence of 5-methylcytosine is based on the specific reaction of bisulfite with cytosine. The latter is converted under appropriate conditions into uracil, which, as far as base pairing is concerned, is equivalent to thymidine, and which also corresponds to another base. 5-Methylcytosine is not modified. As a result, the original DNA is converted in such a manner that methylcytosine, which originally could not be distinguished from cytosine by its hybridization behavior, now can be detected by "normal" molecular biological techniques. All of these techniques are based on base pairing, which can now be completely exploited. The state of the art, as far as sensitivity is concerned, is defined by a method which includes the DNA to be examined in an agarose matrix, intended to prevent the diffusion and renaturing of the DNA (bisulfite reacts only with single-stranded DNA) and to replace all precipitation and purification steps by rapid dialysis (Olek, A., et al., Nucl. Acids. Res. 24, 5064–5066). Using this method, individual cells can be examined, which illustrates the potential of the method. However, so far only individual regions up to approximately 3000 base pairs in length have been examined, and an overall examination of cells to identify thousands of possible methylation events is not possible. However, this method is not capable of reliably analyzing minute fragments from small sample quantities. In spite of protection against diffusion, such samples are lost through the matrix.

2.8 State of the Art in the Use of the Bisulfite Technique

To date, barring few exceptions, (for example, Zeschnigk, M. et al., Eur. J. Hum. Gen. 5, 94–98; Kubota, T. et al., Nat. Genet. 16, 16–17), the bisulfite technique is only used in research. However, short specific pieces of a known gene after bisulfite treatment are routinely amplified and either completely sequenced (Olek, A. and Walter, J., Nat. Genet. 17, 275–276) or the presence of individual cytosine positions is detected by a "primer extension reaction" (Gonzalgo, M. L. and Jones, P. A., Nucl. Acids. Res. 25, 2529–2531), or enzyme cut (Xiong, Z. and Laird, P. W., Nucl. Acids. Res. 25, 2532–2534). All these references are from the year 1997. The concept of using complex methylation patterns for correlation with phenotypic data pertaining to complex genetic diseases, much less via an evaluation algorithm such as, for example, a neural network, has, so far, gone unmentioned in the literature; moreover, it cannot be performed according to the methodologies of the state of the art.

3. PROBLEM OF THE INVENTION AND SOLUTION OF THE PROBLEM

In summary, the state of the art presents weaknesses which are solved by the method according to the invention.

The problem is solved by a method for the characterization, classification and differentiation of tissues and cell types, for the prediction of the behavior of tissues and groups of cells, and for the identification of genes with modified expression, characterized in that:

in genomic DNA, which has been obtained from any tissue sample, and which may have been treated, subjected to shearing, or cleaved by means of a restriction endonuclease in a manner which in itself is known, the base cytosine, but not 5-methylcytosine, is converted by treatment with a bisulfite solution into uracil, in a manner which in itself is known, fractions of the so-treated genomic DNA are amplified by the use of either very short or degenerated oligonucleoticles, or oligonucleotides which are complementary to adaptor oligonucleotides, that have been ligated to the end of the cleaved DNA before the bisulfite treatment, overall, the quantity of the remaining cytosine on the guanine-rich DNA strand, and/or guanines on the cytosine-rich DNA strand from the amplified fractions, are detected by a hybridization or polymerase reaction which is such that the data generated in such an analysis, automatically applied to a processing algorithm, make it possible to draw conclusions regarding the phenotype of the analyzed cell material.

According to the invention, it is advantageous for the data obtained from this analysis of several or many such tests on DNA samples from phenotypically identical or similar cells or tissue to be correlated in a training phase using a neural network or other evaluation algorithm with the phenotype of the cells, whose DNA was examined, the data included in this training phase in the evaluation pattern on the connection between the phenotype and the methylation state to be used for deriving, by the generation of a methylation state of a DNA sample of unknown origin, the phenotype of the cells whose DNA was examined, or the data included in this training phase in the evaluation pattern on the methylation state, of the DNA of a known cell type, to be used for identifying cytosine positions which differ in the examined DNA from the methylation state determined in the training phase.

Furthermore, it is advantageous, according to the invention, to cleave the DNA before the treatment with bisulfite and restriction endonucleases that contain cytosine in the 5'-CpG-3' context in their recognition sequence, and to cleave the DNA cleave at those recognition sequences in which cytosine, in the 5'-CpG-3' context, is in the unmethylated form in the 5' position.

Furthermore, it is advantageous, according to the invention, that before the genomic DNA is modified, in a manner which in itself is known, with a bisulfite solution, this genomic DNA is cleaved with a restriction endonuclease, the resulting ends are provided, by means of a ligation reaction, with known, short and double-stranded DNA sequences, also called adaptors, oligonucleotides, which are complementary to the adaptors that have been treated with bisulfite, are used for the purpose of amplifying all of the DNA fragments or subpopulations thus generated, from the totality of all the fragments produced in this manner, after a treatment with bisulfite.

In this context, it is advantageous that the reaction of a genomic DNA probe with a bisulfite solution for the conversion of cytosine to uracil takes place with simultaneous maintenance of methylcytosine under cyclic variation of the reaction temperatures between 0° C. and 100° C.

It is also preferred that the DNA, before the treatment with bisulfite, is cleaved into a heatable porous capillary that is only permeable to small molecules, in which the following reaction steps of the bisulfite treatment are carried out by adding and removing reagents by dialysis.

Furthermore, it is advantageous, according to the invention, to transfer the sample before the treatment with bisulfite into a heatable capillary that is not permeable to small molecules, in which the following reaction steps of the bisulfite treatment can be carried out by the addition and removal of the reagents by supplying reagents through connected capillaries.

Furthermore, it is advantageous, according to the invention, that the polymerase reactions which follow the bisulfite treatment are carried out in the same capillaries as the bisulfite treatment or in a capillary connected to this capillary, or in a container connected to this capillary.

It is also advantageous that, in a capillary in which the polymerase reactions are carried out with a DNA sample treated with bisulfite, a separation by length of the fragment population produced is carried out.

Furthermore, it is preferred that a treated DNA be separated by separation of the bisulfite from the latter.

Furthermore, it is preferred, according to the invention, that, for the amplification of the genomic DNA samples treated with bisulfite, oligonucleotides of two classes are combined, where the oligonucleotides of one class do not contain the base cytosine or analogs thereof, except in the 5'-CpG-3' context, or to only a very small degree, or only in regions of the oligonucleotides that are not essential for amplification, and where the oligonucleotides of the other class do not contain the base guanine or analogs thereof, except in the 5'-CpG-3' context, or to only a very small degree, or only in regions, such as, for example, the 5' regions, of the oligonucleotides which are not essential for amplification, and where the two classes of oligonucleotides either a) are so short that, in an amplification where each contains only one representative of the two classes, more than 100 different fragments are amplified, or b) these oligonucleotides contain so many so-called degenerated positions that, in an amplification with only one representative of each of the two classes, more than 100 different fragments are amplified, or c) so many representatives of both classes of oligonucleotides are used in an amplification that more than 100 different fragments are amplified.

It is advantageous to consider it optimal to mix the treated and amplified DNA in separate preparations for the purpose of a polymerase reaction with different oligonucleotides in each reaction which are complementary at their 5' termini to the adaptors or generally complementary for the amplification of the oligonucleotides treated with bisulfite, and which are different at their 3' termini in each reaction, and whose variable 3' termini start downstream of the known adaptor sequence or oligonucleotide sequence, and their variable 3' termini extend beyond the known adaptor sequence by between 2 and 12 nucleotides into the unknown template DNA sequence.

In this context, it is again particularly preferred that such reactions, in which a polymerase reaction with oligonucleotides is started, which oligonucleotides are complementary to DNA treated with bisulfite, contain, in addition to the three nucleotides dATP, dTTP and dCTP, or analogs of these three nucleotides, a nucleotide analog that is complementary to the base cytosine and which, after incorporation by the polymerase, blocks any further elongation of the strand, or no nucleotide or nucleotide analog that is complementary to the base cytosine.

Furthermore, it is here preferred, according to the invention, that such reactions, in which a polymerase reaction is started with oligonucleotides, that are complementary to DNA treated with bisulfite, contain in addition to the three nucleotides dATP, dTTP, and dGTP, or analogs thereof, three nucleotides, a nucleotide analog that is complementary to the base guanine and which, after incorporation by the polymerase, blocks any further elongation of the strand, or no nucleotide or nucleotide analog that is complementary to the base guanine.

It is particularly preferred in this context that the termination of a polymerase reaction occurs at the positions which earlier contained methylcytosine in the sample, by means of terminators which themselves have been modified in such a manner that they allow the detection of the specifically terminated polymerase reaction products.

Furthermore, it is provided, according to the invention, that the different fragment mixtures of the individual reaction preparations, resulting from an appropriate combination, are applied to individual points of the ion source of a MALDI-TOF or another mass spectrometer, and the fragment composition of the individual reactions is determined by determining the weight of all the DNA fragments.

Furthermore, it is preferred that the different fragment mixtures of the individual reaction preparations resulting from an appropriate combination are applied to individual lanes in gel electrophoresis, and the fragment composition of the individual reactions is determined by measuring the lengths of all the DNA fragments.

Furthermore, it is provided that the oligonucleotides defined according to the invention, with which the polymerase reactions are started, are each coupled with an oligonucleotide having a different sequence and different chemical labels, and that their chemical and/or physical properties allow the detection and differentiation of the different labels by standard chromatographic or mass spectrometric procedures.

In this context, it is particularly advantageous that the fragment fraction, prepared in the first amplification step, of the DNA to be examined which has been treated with bisulfite, is mixed simultaneously with two or more chemically differently labeled oligonucleotides, these oligonucleotides are used in a reaction preparation as primers for a polymerase reaction, the resulting complex mixture of fragments is subjected in a first analytical step to an electrophoretic separation by length, and the individual length fractions of the fragment mixtures resulting from the electrophoresis are subjected to a chromatographic or mass spectrometric analysis, which detects, in each length fraction, the presence or absence of the chemical labels that characterize the oligonucleotides.

Furthermore, it is provided according to the invention that, onto a surface, oligonucleotides are applied which either do not contain the base cytosine or analogs thereof, or only in the 5'-CpG-3' context, or only in regions which are not essential for hybridization with sample DNA, or which do not contain the base guanine, or contain it only in the 5'-CpG-3' context, or in regions which are not essential for hybridization with sample DNA.

In this context, it is preferred, according to the invention, that the DNA sample which has been treated with bisulfite and amplified is hybridized with oligonucleotides that are fixed to a surface in a known manner so that it is known, for each point of the surface, which oligonucleotide sequence is located precisely at that point, a hybridization of the amplified sample DNA with the fixed oligonucleotides occurs, or persists only after appropriate washing steps, if oligonucleotides and the sample DNA are completely complementary in the regions that are essential for a hybridization.

An additional object of the present invention is a kit, characterized in that at least two of the components defined above (for example, a combination of oligonucleotides for the amplification of DNA that has been treated with bisulfite and oligonucleotides fixed to a matrix for protection) are combined for treatment of DNA with bisulfite, amplification of this treated DNA, and resulting detection of the methylation state of more than 100 CpG dinucleotides of a mammalian genome in a reaction such that a clinically relevant diagnosis of a cancer disease can be made.

The method solves the problem of determining parameters which are diagnostic for the behavior of cells in extremely large quantities. For this purpose, a completely new concept of cell analysis must be elaborated, a completely new evaluation mechanism must be connected with this analysis, and, furthermore, the technical basis for the generation of data must be made available. The method uses, for the first time, the information content of the cytosine methylation, and thus it makes available the analytical methods and associated evaluation algorithms required for that purpose. The method according to the invention is therefore used for the purpose of finding, in the case of cells affected by heritable defects, secondarily involved gene loci which, using the methods according to the state of the art, either can theoretically not be determined, or only with very great difficulty: the method presents genetically modified loci, whose (possibly epi-)genetic changes do not contain any actual changes in the base sequence. In this manner, the method according to the invention makes available targets for new therapeutic strategies. The method furthermore solves the problem of classifying degenerated cells in such a manner that considerably more or more precise correlations are established between the (epi-) genotype and the phenotype than is possible in the state of the art. The method according to the invention, in addition, allows the prediction of the probable future behavior of degenerated cells and the reactions of such cells to stimuli from within or outside of the body. Finally, the method also aids in choosing the best therapeutic methods for cancer diseases. Furthermore, the method allows the determination of shared genetic and/or biochemical features of tumor cells, which are phenotypically similar, but genotypically different (to the extent that differences can be determined by the state of the art). The assumption on which this claim of the method is based is that the most different genotypes can lead to very similar epigenotypes, and thus to very similar phenotypes. Consequently, the proposed method is also capable of detecting such changes in the genetic expression of tumor cells, which are not caused, or only indirectly caused by changes in the base sequence.

4. DETAILED DESCRIPTION TO THE SOLUTION OF THE DEFINED PROBLEM BY THE METHOD ACCORDING TO THE INVENTION

The proposed method solves defined problem in an innovative manner by the combination and improvement of different methods of the state of the art. Certain modifications, according to the invention, of these methods, which in themselves are known, serve the purpose of adapting them to the new requirements, so that a completely novel overall method is produced, which will be described below with reference to preferred variants of the method, and which will be described by means of examples.

4.1 Preliminary Treatment of the DNA Sample for Treatment with a Bisulfite Solution Fundamental process steps, such as the isolation of tissues or cells, and the extraction of DNA from the latter, are carried out in a manner which in itself is known. However, the extraction of DNA for further analysis will take place in the case of the preferred variants of the method in a minute volume, usually, like the treatment with bisulfite itself, in a layer of oil, which prevents contact with the environment. The purpose of this approach is to keep the losses of DNA so low that a reproducible result is guaranteed even with exceedingly small starting quantities. The extraction of the DNA from the cells or tissues can also take place directly in a capillary, as described below, in which all subsequent reactions can then be carried out. A limitation of the extraction volume is, however, not a necessary component of the proposed method.

Extracted DNA can now be subjected to bisulfite treatment in untreated form, to shearing, or specific cleavage with restriction endonucleases.

The method according to the invention, at this point, can be subdivided into two different method variants. One variant, in which the last detection of the individual methylcytosine positions is performed by a hybridization with oligonucleotides, usually requires, at this point, no additional preliminary treatment of the DNA. A second variant, characterized in that the genome-wide amplification of the DNA samples is carried out via an oligonucleotide, with samples that are complementary to the adaptors, which are ligated to the end of the DNA and treated with bisulfite, requires the ligation of such adaptors to the individual fragments of the cleaved DNA. The adaptors are short, double-stranded DNA molecules, presenting, as a rule, a single-stranded projection. This projection is complementary to the ends of the cut DNA samples, so that, at both ends of the DNA fragments of the sample, such an adaptor can be attached by means of an appropriate ligase. For this purpose, quantities of adaptors must be added which are such that they are present in an excess with respect to the number of fragment ends. The ligations of adaptors to sample fragments can, however, in principle, also be carried out without complementary single-stranded projections. The individual reactions are, in principle within the state of the art (Sambrook et al., Molecular Cloning: A laboratory manual, CSHLP, 1989), and they will therefore not be described further. The combination of the ligation of adaptors with the bisulfite treatment and subsequent genome-wide amplification is, in principle, innovative, and it is not mentioned in the literature or patent literature.

4.2 Modifications According to the Invention of the Bisulfite Method

The foundation of all the variants of the method according to the invention is the method of the modification of single-stranded DANN [sic; DNA] with bisulfite. In order to make possible some of the variants of the method according to the invention, some modifications of the bisulfite method are, however, required.

The principal variants of this method are based, on the one hand, not only on the fact that total quantities of starting materials should be minute (in the limiting case, only one cell or several tens of cells), but also on the fact that several variants of the method, in fact, require the use of minute fragments. In addition, the routine application of the method according to the invention for clinical diagnosis requires the automation of all the process steps in such a manner that as high a degree of reproducibility as possible can be achieved.

All the steps of the bisulfite method should therefore be carried out in minute volumes, with complete protection from the "outside world." The inclusion of the bisulfite reaction in an agarose matrix here already constitutes progress with respect to the diffusion of fragments, but, the reaction still takes place in a very large volume of aqueous bisulfite solution. As a result, small important DNA fragments can diffuse into the solution and thus become lost to further analysis.

The method according to the invention includes the implementation of the bisulfite method without using any external volume. For example, the bisulfite reaction is carried out in oil in a volume of only 1–10 mL, and all the components can thus be pipetted directly by a robot under the oil, where they form a single drop, in which all subsequent reaction steps tale place. The difficulty of preparing a bisulfite solution with the concentrations required according to the state of the art, and the fact that the solution of this dilemma according to the state of the art, using lower reaction times with lower bisulfite concentration, results in significant damage to the DNA sample, is solved by the method according to the invention.

This method uses the fact that the different reaction steps of the bisulfite reaction are equilibrium reactions. These equilibria are on the correct (sulfonated and deaminated) side at different temperatures, for the two important reaction steps, the sulfonation of the cytosine and the subsequent deamination. If one takes into account the kinetics that apply to the establishment of the individual equilibria, then it is apparent that it is advantageous to carry out the bisulfite reaction under cyclic conditions, with changing temperatures. A preferred variant of the method comprises a change from 4° C. (10 min) to 50° C. (20 min). All the other temperatures, and reaction times at certain temperatures, however, should be included in the method according to the invention. For example, under certain conditions, it has been advantageous if considerably shorter reaction times are regulated. It is also useful, and in principle novel, to insert a step at which the DNA to be examined is again denatured at very high temperature, between a deamination step (at high temperature, $\geq 50°$ C.) and a subsequent repeated sulfonation step. For high molecular weight DNA, the denaturation temperatures are, as a rule, >90° C., but they can also be lower, and still be within the scope of protection of the method. There are two reasons for this. On the one hand, variants of the method exist in which very short DNA fragments are examined. On the other hand, in each reaction cycle, as a result of the conversion of cytosines to uracils which has occurred, the complementarity between strands decreases. Therefore, a cyclic reaction protocol can have a very complex appearance. For example, in the first cycles, the denaturation temperature can be higher than 90° C., but in later cycles it can be regulated to lower values. Multistep reactions, in all situations, can only be optimized by performing extremely involved test series. Therefore, the claimed protection should relate generally to cyclically performed bisulfite reactions.

An additional solution of the above-mentioned problems in the state of the art is based on the transfer of one or more steps of the method to a capillary. In principle, there are two variants: the capillary can be 1) impermeable, or 2), it can be permeable for certain solvents like a very thin dialysis tube.

The variant according to 1) indicates that a drop, as described in the above examples, with DNA, bisulfite and radical interceptor can be introduced into an aqueous solution from outside by means of a heatable and coolable capillary. In this process the drop can be isolated by a fluid or a gas phase within the capillary. All the reactions then take place within this capillary, and additional reagents can be added through inlet connectors. Because this capillary according to variant 1) is completely closed to the outside, it is necessary to add a matrix solution for the subsequent steps, which results in the above-mentioned problems and requires solutions according to the invention.

The variant according to 2) indicates that, at first only the DNA solution is led through the porous capillary, which has been pretreated by a corresponding preliminary treatment using process steps according to the invention or other process steps. The capillary itself is led through solutions, from containers, which are required for reaction steps within the capillary. In concrete terms, the DNA solution within the capillary, in the case of this variant, is first led through a bisulfite solution, which, in addition, can be subjected to cyclic temperature changes or constant temperature. In an additional step, after completion of the bisulfite reaction, the capillary is led through a dialysis solution, then through an alkaline solution, and finally through an additional dialysis solution. After these steps of the bisulfite treatment in the capillary, an additional variant of the method is provided, where all other PCR and primer extension steps are performed in the same capillary. In the case where the different primers for the primer extension according to the invention arc labeled by a special chemical modification, a capillary electrophoresis can also be carried out, directly after all these PCR and primer extension steps, in an elongation of the same capillaries. In the electrophoresis, the extension products are separated by length, and a subsequent mass spectrometry, chromatography, or optical analysis then separates the collected size fractions by their label, thus generating the result spectrum or result chromatogram in the second analysis dimension.

The use of a capillary for the bisulfite and PCR and/or extension reactions also simplifies the use of another detection variant according to the invention. Indeed, the fragments can be led immediately after the amplification into a capillary which as described further below, carries on its internal side the oligonucleotides, specific for the individual methylcytosines, as hybridization partners.

An additional variant of the method is based on an elimination of the high molecular weight bisulfite solution, other than by dialysis. The advantages of this variant eliminate an additional drawback of the variants described thus far.

Every dialysis in agarose allows parts of the procedure to take place in a large volume of aqueous solution. As a result, there is a risk of loss of DNA fragments due to diffusion. One problem with variants that occur in a capillary is that a small percentage of DNA fragments, which, in the case of minute quantities of DNA, may be significant, can bind to the internal wall of the capillary and thus become lost for the analysis.

Therefore, the following method is proposed: The DNA extraction is carried out, as described, in a minute volume under an oil layer. In the preferred variant of the method, the volume is 1 $\mu L$. Naturally, the method is not essentially changed by the use of smaller or larger volumes. Thus, these methods also fall within the claimed protection scope. The DNA is denatured (as mentioned). The required bisulfite concentration is then added by the addition of a larger volume of a bisulfite solution (for example, 4 $\mu L$), which is slightly larger than necessary for the proper treatment, so that the required final concentrations and pH become automatically established under the oil. Subsequently, the bisulfite reaction is carried out in one of the described manners.

In the next method step (in a preferred variant of the method according to the invention) a small molar quantity of a salt, for example, barium hydroxide, is added to the solution, whose cation forms an insoluble salt with the bisulfite and thus precipitates out of the solution. The addition of this solution also effects an increase in the pH to values at which the desulfonation of the cytosine, that was sulfonated and deaminated in the first reaction steps, can take place. During the desulfonation reaction, which takes place very quickly, the precipitated bisulfite salt can be separated by a brief centrifugation from the aqueous sample solution. Ilowever, it is preferred to use a salt which has the following properties. The cation forms a salt with a bisulfite, which salt remains insoluble even under the conditions of the amplification process, and which in no way has a detrimental effect on the amplification process. In addition, the quantities of none of the ions, which do not precipitate out of the solution in such a process, must be such that the quantities in which the ions are then present impede the amplification process. The possible interference of such salts in the amplification process can, however, also be circumvented by using extremely precisely prepared salt solutions, which can also be pipetted with extreme precision. The use of identical quantities of salts leads to a quantitative elimination of the potentially interfering ions. The use of potassium bisulfite and other counterions complementary to the subsequent amplification buffers also simplifies the buffer changes described below for the amplification reaction.

In the next method step, an additional volume of a solution which has the following properties, is added under the oil. The salt composition is such that, during the mixing with the solution of the treated DNA located under the oil, salt concentrations and pH values are reached which allow an enzymatic amplification process. In this context, all thermostable polymerases of any origin can be used. The type of the polymerase used is not essential, and it can also be varied depending on the existing buffer conditions, and thus protection is claimed for the use of all such polymerases. Secondly, this solution contains such a polymerase, all the nucleotides and the required oligonucleotide primers. After the addition of this solution, an amplification can thus take place directly in the same reaction vessel. In this manner, no contact with the "outside world" is possible during all the process courses; not even the slightest amount of sample can be lost.

4.3 Genome-Wide Generic Amplifications of Bisulfite-Treated DNA

The detection of thousands to millions of methylcytosine positions in each case requires the amplification of a large percentage of all the possible sequences of a sample genome. This part of the method according to the invention should be subdivided, as was already done in the section "preliminary treatment," into two variants which differ in principle.

The first variant of these process steps is based on the ligation of adaptors to the fragmented DNA before the bisulfite treatment. In the simplest form, an oligonucleotide is used for this purpose that is complementary to the adaptor sequences and present after the bisulfite treatment. In this process, this oligonucleotide can hybridize with any region of the adaptor sequence. In the case of a polymerase reaction with these components, this theoretically leads to an amplification of all fragments with adaptors at both ends. For example, this could be all of the fragments which produce a prior cleavage with restriction endonuclease. However, for some variants of the method it is necessary, because of the limited number of the individual fragments produced by one such amplification, to subdivide the reaction into different partial reactions after a small number of amplification cycles. These partial reactions can now be carried out with oligonucleotides, a few of which extend beyond the adaptor sequence proper, namely by one to four bases, into the unknown sequence of the different fragments. The oligonucleotides of the different reactions are chosen in such a manner that each one covers a part of all possible unknown sequences, such that the totality of all these oligonucleotides in the different reactions covers all possible sequences which theoretically can be located behind the known adaptor sequences. For example, four reactions can be set up, where the oligonucleotide of the first reaction at the 3' terminus, after the known adaptor-complementary sequence, contains the base adenine, the second cytosine, the third guanine, and the fourth thymidine. Naturally this principle can also be applied with more than four different reactions, where the sequence at the 3' terminus of the oligonucleotide then comprises more than one base. Here the positions at the 3' terminus of the oligonucleotides can also present so-called degenerated positions. This means that, in one position, more than one base with similar efficiency is linked to the oligonucleotide, or two or more oligonucleotides are mixed with nondegenerated sequence. Thus, all possible sequences can be covered with total numbers of reactions which are not powers of the number four.

In this manner, in each reaction, a subpopulation of all the fragments can be amplified, resulting in a higher reliability and higher amplification of the individual fragments. In principle, a step-wise subdivision of the reaction is also possible, so that a first number of amplification cycles is carried out with only one oligonucleotide covering all sequences, and the subsequent reaction is subdivided, for example, into four reactions with one specific 3' base per reaction, and followed by several additional amplification cycles, which in turn arc followed by one or more subdivisions. An essential point here is the precise measurement of the quantity of the oligonucleotides added. Ideally, a quantity of the oligonucleotide is added to each series of amplification cycles, which is such that it is completely or almost completely used up during the reaction. Then the reaction mixture of every cycle can be transferred directly and automatically to additional steps.

The alternate variant, with a different principle, does not need a prior ligation of adaptors to precut DNA. In the state of the art, several methods are prescribed which achieve genore-wide amplifications of DNA with varying decrees of success. All of these methods have to be changed for the method according to t he invention. We have tested the use of three different methods. First, and as a preferred variant, we use a modification of the described "DOPE" technique. In contrast to the method mentioned in the literature, We use two or more different oligonucleotides in each amplification, which oligonucleotides can be subdivided into two classes. These classes are characterized in that in one, the base guanine, and in the other, the base cytosine, is not represented, or hardly represented, or only represented in a 5' region. If these bases arc present at all in the sequence of these oligonucleotides, then they are normally in the context of the 5'-CpG-3' sequence. The purpose of this is that each of these classes of oligonucleotides hybridizes on the two (G-rich) strands present after the bisulfite treatment, or the (C-rich) counterstrands copied by means of the polymerase reaction from these strands. By the combination of representatives of these two sequence classes, it is therefore possible to achieve an amplification of bislfite-treated DNA. Cytoslines outside of the 5'-CpG-3' sequence should be converted in the template DNA to uracil in most cases, so that no guanine is required for an efficient amplification in the oligonucleotide which hybridizes with the bisulfite-treated strand. On the counterstrand, the same applies to guanine. If, in these classes of oligonucleotides, guanine or cytosine is present in a 5-CpG-3' context, then this leads to the possibility that these oligonucleotides can also hybridize with potentially menthylated positions. For the proposed method, this is of no use. However, it can happen that the drawbacks are so small that considerable components of the method can also be implemented in this manner. Therefore, the scope of protection should also include such oligonucleotidcs. It is equally conceivable, although it would in principle tend to be damaging for the efficient implementation of the method, for individual guanines to be present in positions outside of the 5'-CpG-3' context. Normally this leads, during the hybridization of the oligonucleotide with a target DNA, required for the amplification, to positions that are not base paired, which in most cases reduces the efficiency of the amplification and is therefore not desirable. Nevertheless, the amplification with oligonucleotides which contain one or a few guanine bases from this strand is possible, although not ideal. Since such an amplification could still fulfill the essence of the invention, the utilization of such oligonucleotides, which because of the use of several guanines do not strictly fall in this class, should also fall within the scope of protection. It is particularly the second technique that we used which requires exceptions of this type. In this technique, oligonucleotides are used which, in principle, in their 3' region, fall into one of the described sequence classes. In the 5' region of these oligonucleotides, a so called "sequence tag" is, however, attached, which is used in subsequent steps for further amplification. In this variant, in the first cycles of the amplification, the 3' region of the oligonucleotides, which fall in principle into one of the above-mentioned classes are used to amplify a large spectrum of fragments. In subsequent steps, each fragment amplified so far has at the 3' end a sequence which corresponds to the sequence tag. These sequences can then be used, analogously to the amplification by means of oligonucleotides which are complementary to the adaptors, as a hybridization partner for an oligonucleotide, which is used for additional amplification. Naturally, the sequence tag of this first oligonucleotide can contain guanine in the 5' region of oligonucleotides belonging in the 3' region to the first class, and cytosine in the 5' region of those belonging to the second class.

Oligonucleotides, or oligonucleotides which, according to their 3' regions, belong to one of the two classes, can be constructed differently. Our variant of the DOPE method uses a combination of oligonucleoticles of the two sequence classes, which present, in the 3' region, a predetermined base sequence. This base sequence can, within the method according to the invention, have a length between 2 and 20 bases. Before this sequence, a usually 5–20 base long section of "H" positions is located in the first class, and "D" positions in the second class. This means in these positions, in the synthesis of the oligonucleotide, one of the three bases A, C or T was incorporated in the case of class "H," and one of the bases A, G or T in the case of class "D" (where the above mentioned exceptions, which do not affect the essence of the invention, should be included in the protection). Before this section (5'), an additional section with a specific sequence can (but does not have to) be located. If these oligonuclcotides are used under the corresponding conditions for the amplification of bisulfite-treated DNA, then a fraction of the entire genome, which can be defined over the specific regions of the oligonucleotides, can be amplified in a reproducible manner. In the case of the use of sequence tags, the 5' region of the oligonucleotides can present a defined sequence, which breaks through the definition of the two sequence classes. Oligonucleotides should also be included in the scope of protection for the purpose in the overall method if the oligonucleotides contain regions "H" and "D" in the 3' region, or if they contain positions of defined bases which alternate with those of the classes "H" or "D" in any form.

Furthermore, the scope of protection should also include oligonucleotides used as amplification primers, which are used within the overall concept of the method and which form "hairpin" structures at their 5' terminus, molecules which present a base pair behavior which is analogous to the base pair behavior implicit in the above description, such as, for example, oligonucleotides based on PNA (protein-nucleic acid), chemically modified oligonucleotides: and modified or unmodified oligonucleotides which were synthesized with nucleotides other than the natural nucleotides.

4.4 Detection of the Methylation State of CpG Dinucleotides 4.4.1 Detection of Methylated CpG Dinucleotides on DNA Chips In its final form, it is possible that the method according to the invention will be based on the use of a DNA chip. Therefore, the use of a DNA chip presents a preferred variant of the method. In principle, all the described variants of the method are possible up to the amplification of the bisulfite-treated DNA. A chip used for the implementation of the method, in the preferred variant, has the following form: On one of the surfaces provided for this purpose, at least one thousand, and as a rule, more than one hundred thousand, oligonucleotides are synthesized in situ in a known manner, or applied with a micropipette or nanopipette, a stamp-like apparatus, or a microfluidic network. Each oligonucleotide is specific for one CpG position; this means that it either hybridizes only with the target DNA if the CpG position contained in the oligonucleotide is methylated, or only if this position is specifically unmethylated. Therefore, for each position, at least (see below) two oligonucleotides can be applied. The number of different oligonucleotides has no upper limit, and it can even be larger than eight times all the CpG dinucleotides contained in the genome. It is known, for every point of the DNA chip, precisely what oligonucleotide sequence is located there.

The method according to the invention leads to an essential modification in the normal occupation of such a DNA chip. On a DNA chip according to the state of the art, oligonucleotides are located which are complementary with genomic or expressed sequences. This means that all the oligonucleotides, on average, correspond to the base composition of the genomic DNA or that of the expressed sequences of an organism. For most oligonucleotides located on such a DNA chip, that is, all four bases, on average, the proportion of guanine and cytosine bases corresponds to that of the genomic and/or expressed sequences.

This situation is different in the context of the method according to the invention. In principle, eight classes of oligonucleotides can be synthesized for each sequence covered by oligonucleotides. As a result of the bisulfite treatment, the DNA is modified in such a manner that the originally complementary top and bottom strands (Watson and Crick strands, also called coding and template strands) are now no longer complementary. This means that oligonucleotides for both strands can be synthesized. This possibility exists because the two strands can be used in this manner as internal controls for each other. The hybridization behavior of the two different strands with the oligonucleotides that fit in each case is different because of the partially significant differences in sequence. The result of this is that, when the same result is achieved on both strands, this can be considered to have been independently confirmed. The quantities of methylcytosine and cytosine at each position to be tested should also be quantified. The use of both strands allows, as a result of the evaluation of different hybridization events for each individual CpG position, a quantification of the data which is independent of the different hybridization parameters of the oligonucleotides. Background errors are thus minimized.

After the bisulfite treatment, not only are the two strands different, because, after the treatment, an amplification is carried out in each case which effects at each one of the two strands again the new synthesis of a complementary counterstrand. Just like the original strands are not complementary to each other after a bisulfite treatment, the two counterstrands are also not complementary to each other. A counterstrand which is newly synthesized during the amplification is also not complementary to the originally different strand (the one at which the counterstrand was not synthesized). Thus, two different hybridization targets are produced for each individual CpG position. These four strands all contain (here we assume symmetric methylation, that is, methvlation at both strands of a CpG position) the same information, but they hybridize with oligonucleotides having different sequences. In this manner, every piece of information obtained on any CpG position is confirmed four times independently. Nevertheless, the signal strength for the four different oligonucleotides cannot be correlated directly (except in the case of experimental values generated by the use of the system) with the degree of methylation of a position. Indeed, the situation is such that different fragments are also amplified with different efficiencies in an enzymatic amplification, and thus the strength of a signal does not necessarily correlate with the degree of methylation, rather it also correlates with the efficiency of the amplification of the fragment containing the CpG position. Therefore, in every case, both possible oligonucleotides for all four strands must be analyzed, on the one hand, the oligonucleotide which hybridizes only if the CpG position to be examined is methylated (which contains CpG) and, on the other hand, the oligonucleotide which hybridizes only in the case of an unmethylated CpG position (which thus contains no CpG). The two possible variants of a DNA strand, namely the methylated and the unmethylated variants, are amplified at largely identical efficiency, and thus allow a comparison. Since complementary information is now available for all four strands, all four strands can also be used to corroborate the overall result. In the context of the method according to the invention, the main criteria which distinguish the oligonucleotides from other methods are that they contain, in each case, only three of the four bases. The oligonucleotides which are complementary to the original DNA strands only contain the base C, and not the base G. Only half of all these oligonucleotides contain precisely one guanine, namely in the CpG context precisely at the location whose methylation state is to be tested. The second class of oligonucleotides, which is complementary to the counter-strand of the original DNA, which is generated in the amplification, in contrast contains the base cytosine only in those locations whose methylation state is to be tested.

Those oligonucleotides, which hybridize only with the target DNA if the position tested by them is unmethylated, contain (depending on the strand) either no cytosine or no guanine. Naturally, within the proposed method, the described eight classes of oligonucleotides can also be variable in other regards. It is also possible to use several representatives of one class simultaneously for the examination of each individual position that can be methylated. For example, it is not obvious in every case how many bases are included on each side of the potential methyl position on each side in the oligonucleotide. The position that can be methylated does not have to be precisely in the middle of the oligonucleotide. Therefore, many permutations are possible for each position to be tested.

In the extreme cases, the position to be tested is located at one of the ends of the oligonucleotide or (although this is already a component of an additional variant of the method), even one position behind the 3' terminus, so that the presence of cytosine or guanine (and thus of methylation of the original sample) is detected not by simple hybridization, but by the detection of a primer extension. In this variant of the method, modified nucleotide triphosphates (in such a manner that, although the incorporation of such a nucleotide at the 3' end of a primer is possible, no additional elongation past this nucleotide is possible. As a rule, 2',3'-dideoxy analogs of the four nucleotide triphosphates are used here), with a different labeling for each one of the four nucleotides, are added to the target DNA, which is then hybridized on the chip with the oligonucleotides. Instead of then detecting the hybridization directly, a polymerase is added, and at each position precisely one nucleotide is synthesized at the 3' end of the oligonucleotide. The nucleotide which is complementary to the nucleotide incorporated at the 3' end of the nucleotide precisely corresponds to the nucleotide which is located on the target DNA hybridized with the oligonucleotide one 5' position before the oligonucleotide. In our method, this position is a position in the original DNA, which can be methylated. Thus, when (depending on the strand) the position in the DNA sample was methylated, then a C is located at this position; a G is then "added" to the oligonucleotide. If the dGTPs (or analogs of this nucleotide) are now unambiguously labeled, and (this is a prerequisite) the oligonucleotide sequences at all positions are known, then, in this case, the detection of the incorporation of guanine can be used to detect the presence of a methyl group in the original sample. If an adenine is attached to the same oligonucleotide, then the detection of thymidine has succeeded, and, by the same token, the demonstration has been made that the examined position was unmethylated. The same demonstration, except with the labeled ddNTPs cytosine and thymidine, can occur on the counterstrands prepared in the amplification. In this variant of the method, the oligonucleotides of both sequence classes either contain no cytosine or no guanine. Nevertheless, this rule can be broken in exceptional cases (for example, when it is known that one position is always methylated or always unmethylated, or if the methylation state of the position has no influence on the hybridization behavior of the oligonucleotide). Furthermore, one or several "mismatch positions" within the oligonucleotide, in spite of the fact that they in principle have a harmful effect, can meet essential requirements of the method. Oligonucleotides which do not belong, strictly speaking, in the sequence classes, but which fulfill essential components of the method, should therefore be included in the patent protection. In addition, the attachment of the oligonucleotides to the surface of the DNA chip can take place via sequence tags on the oligonucleotides, which are complementary to a generic sequence of oligonucleotides attached to the surface. Such oligonucleotides belong to the defined sequence classes only in the regions available for the hybridization with the DNA sample. Furthermore, oligonucleotides that are used as hybridization partners on the surface of DNA chips should also be included in the scope of protection, if they present a base pair behavior which is analogous to the base pair behavior implicit in the above description, such as, for example. oligonucleotides based on PNA (protein-nucleic acid), chemically modified oligonucleotides and modified or unmodified oligonucleotides which were synthesized with nucleotides other than the natural nucleotides.

Naturally this applies to all the variants of the method, which are based on the hybridization of oligonucleotides directly with the position to be tested or with only one base on the primer extension: As a rule, only one position is tested, and this position also comprises the entire cytosine or guanine content of an oligonucleotide. Nevertheless, exceptions to this rule can be of no consequence in individual cases, and therefore they arc also an object of the present invention.

The detection of the different labeled nucleotide analogs in a primer extension reaction on a DNA chip (which may be degenerated to any extent) can also be effected in a great variety of manners. A preferred variant is the detection, in a manner which is known, using a CCD camera, which registers fluorescent signals which indicate that a (naturally fluorescence-labeled) nucleotide has been bound to the chip. In this context, in the above-described variant of the method, each one of the nucleotide analogs is labeled with a different color, so that it is possible to detect which nucleotide has been incorporated in each position.

However, another important variant consists in labeling each one of the four nucleotide analogs with a chemical molecule, which then is separated by exposure to laser firing of a MALDI-TOF from the nucleotide photochemically (or by the heat generated, or an analogous process), and it is then directly ionized and its molecular weight is determined. The laser of the MALDI-TOF apparatus can be targeted with precision onto each position of the chip, and thus it can also determine, for each position on the chip, which weight modification occurred at the location in question. Often (because inethylated and unmethylated target DNA in this variant hybridize with the same oligonucleotides, and the methylation state is determined by the labeling of the incorporated nucleotide), two labels are detected at each position (this naturally also applies to fluorescence labels), and the two signals must be quantified and compared to each other to determine the methylation degree.

However, in the variant of the method which is currently preferred, detection by fluorescence is used. Furthermore, hybridizations are directly detected, and no primer extension reaction is carried out.

4.4.2 Detection of the Methylation State of Cytosine by Mass Spectrometric Measurement of the Lengths of "Primer Extension" Products A variant of the method was developed which allows the detection of very large numbers of cytosines and/or guanines in bisulfite-treated DNA by mass spectromctric measurement of lengths in mass spectrometers based on MALDI. The foundation of this technology, which was modified for this method, has been described above.

In the proposed method we use oligonucleotides which, because they belong to one of the two above-defined sequence classes, hybridized with great probability with only one of the two strands of bisulfite-treated DNA. Oligonucleotides which are used in this variant of the method can achieve the detection of cytosine and/or guanine from amplification mixture prepared by any of the above-described methods of amplification. This means that, in principle, oligonucleotides which are complementary with the adaptors ligated to fragments of the sample before the bisulfite treatment, and also those oligonucleotides which hybridize at undefined positions on the fragments that were amplified in other manners can be used.

The preferred variants of the method contain the use of DNA samples, to whose restriction fragments adaptors were ligated (and then amplified after the bisulfite treatment) or DNA samples which were amplified with oligonucleotides which contain constant sequence tags in their 5' region. The adaptors are synthesized for this purpose in such a manner that, after a bisulfite treatment of the two strands, that is, of the original bisulfite-modified strand and the strand that was newly synthesized during the amplification, their contents with respect to cytosine or guanine differ in such a manner that oligonucleotides for a primer extension reaction can be prepared which specifically recognize one of the two strands. This means that, in this case as well, two sequence classes of oligonucleotides can be distinguished. The oligonucleotides used have the property that their 3' region extends past the known adaptor sequence, past the sequence recognized by the restriction endonuclease, and therefore past the known sequence, into the unknown region of the DNA samples. In case the generic amplification, as described above with step-wise elongation of oligonucleotides, is carried out in serially subdivided separate reactions, then the oligonucleotides defined here also extend beyond this known region. In this context, the oligonucleotides can extend by 2–20 bases into the unknown region. The mixing of the fragments from the first, or from the first generic amplification, is now subdivided, and mixed with different oligonucleotides for each (sub)reaction. In each subreaction it is known here which oligonucleotide is added, and the subreactions differ only in the sequence of the oligonucleotides that have to be added. It is not essential here whether the sequence of the oligonucleotides is defined with precision, or whether individual positions are occupied with the above-defined degenerated nucleotide positions "H" or "D." The use of degenerated positions allows the use of longer regions, which extend into the unknown region, and thus it allows a possibly more precise regulation and incrementation of the number and the type of the extension fragments generated in such a reaction.

With all different subreactions, a polymerase reaction with the following components is carried out. Those reactions which contain oligonucleotides which hybridize with a cytosine-poor strand (corresponding to the original strands of the bisulfite-treated DNA) contain the nucleotides dATP, dCTP, dTTP, and a terminator which is analogous, as far as the base pair behavior, to the nucleotide dGTP, such as, for example, ddGTP or a functionally equivalent nucleotide. The reactions with oligonucleotides of the other sequence class contain a mixture consisting of dATP, dGTP, dTTP and a terminator which is analogous, with regard to its base pair behavior, to the nucleotide dGTP, such as, for example, ddCTP or a functionally equivalent nucleotide. A polymerase reaction is then used to synthesize a new DNA strand, starting with the oligonucleotides, on one (cytosine-poor) strand only up to the first cytosine, and, on the other strand, up to the first guanine.

For analysis by mass spectrometry it is also appropriate to use, instead of naturally occurring nucleotides. nucleotides that have been modified in a known manner by chemical means to facilitate the subsequent analysis by mass spectrometry of the extension products. For this purpose, in our variant, phosphothioate analogs of the natural nucleotides are used. They can be alkylated in a subsequent step, which eliminates the back-loading of the DNA, and increases the quality and the sensitivity of the analysis. However, other modifications should also fall within the scope of protection, if they are made with this purpose. Furthermore, the modification of the loading of the oligonucleotides used, as well as their hybridization properties, can be improved or modified.

The purpose of this variant of the method is the preparation of fragment populations in the individual reactions which are so complex, or only so complex, that they can be separated by gel electrophoresis or more precisely by mass spectrometric analysis by length. As a result, it is necessary to regulate the number of the synthesized fragments, over the length of the part of the oligonucleotides extending into the unknown sequence range, and the degree of degeneration in such a manner that it is, per reaction between one fragment and possibly up to several thousand different fragments.

The individual reactions arc now applied in the preferred variant separately onto defined coordinates of the ion source of a mass spectrometer. The mass spectrometric analysis then determines the fragment spectra for the individual coordinates. In the case of up to several thousand coordinates on the ion source of a mass spectrometer, and several hundred fragments per spectrum, each one of which evaluates a cytosine or guanine position as an indicator of methylation, it is also possible to evaluate up to several hundred thousand individual CpG dinucleotides.

In a similar manner, the detection of fragment spectra generated from a fragment population can also be carried out, which fragment populations were amplified without ligation of adaptors by means of the above-described oligonucleotide primers. In the case of this variant, the sequence that is complementary to the adaptors is omitted, and instead a 5' region containing several degenerated positions is used.

In the case where the bisulfite-treated DNA was preamplified, with oligonucleotides which contain the above-described (5') sequence tag in their 3' region, the DNA can also be used analogously to the adaptor sequences as a constant region for hybridization with oligonucleotides, as described in the section above.

4.4.4 Detection of the Methylation State of Cytosine by the Mass Spectrometric Detection of Chemically Modified Oligonucleotides An additional variant of the method uses a method which, in itself, is known, and which allows the mass spectrometric identification of certain sequences indirectly by the detection of chemical modifications applied to an oligonucleotide.

In the above-described mass spectrometric detection variants, many different primer extension reactions, each with one or several oligonucleotide sequences, is performed. In principle, the extreme number of different analyzable fragments is achieved only by the subdivision into many different reactions (and coordinates on a MALDI ion source).

If a chemical modification is applied to each primer sequence, then, in the case of the use of another analysis technique than MALDI alone, this separation can be omitted.

In practice this means that all the different primers used are provided with such a chemistry already during synthesis, or subsequently; in principle, the chemistry fulfills two requirements. On the one hand, the separation by length of the generated fragment must not be prevented. On the other hand, the type of modification must be able to allow the recognition of the separation by length, in the second analysis step after the capillary electrophoresis. Thus, the type of modification depends on the type of analysis in the second step. In the preferred embodiment variant, the 5' ends of the primer are provided with short peptide sequences, which can be separated in a subsequent step by many conventional analysis methods. One of the great advantages of such a variant is that, even in the first, nonspecific amplification step, a considerably smaller total quantity of DNA must be amplified, because this quantity no longer needs to be distributed over additional reactions. The second dimension of the separation, which is achieved in the above-described variants by the separation into individual reactions, can be achieved in the preferred variant of the method by the implementation of the method according to the invention, where the separation of the generated fragment first occurs by capillary electrophoresis. In this context., it is not essential for a correct result whether the chemical modifications at the fragments influence or do not influence the migration behavior of the fragments, as long as only one separation by length remains possible. In each "fraction," which reaches the end of the capillary electrophoresis, many fragments with the same electrophoretic migration behavior are found, which differ only in the chemical modification of their respective 5' region (in the region of the primer, which was used for the extension reaction). These fragment populations, which are separated according to their electrophoretic migration behavior, are now examined in a second step for the presence of chemical modifications. The preferred variant of the method here is direct injection of the outlet volume of the capillary electrophoresis in a fast atom bombardment (FAB-MS), electron spray ionization (ESI-MS), application onto a MALDI mass spectrometer, or an equivalent analysis apparatus.

In concrete terms, such a variant is carried out as follows, for example. The DNA is prepared as described from cells, precut with a restriction endonuclease, provided with adaptors, and led through a heatable capillary which is porous for small molecules, in which the reaction steps of the bisulfite reaction are carried out by addition and removal of the reagents by dialysis. Here the volume of the overall reaction is minute. After the bisulfite reaction has been carried out, the capillaries can receive, by cross connections with other inlet capillaries, the reagents required for an amplification, and the amplification can then be carried out in the same heatable capillaries. However, it is also possible to carry out the amplification, not directly in the capillary, but in a container connected to these capillaries. After the generic amplification of the genomic fraction, a second linear elongation step is carried out, as described, which is carried out with a mixture of chemically modified oligonucleotides, that consequently can be distinguished by their weight, and that are complementary to the bisulfite-modified adaptors. The next step is the separation by length of the elongation products in an additional section of the capillary and, possibly, an additional dialysis against a buffer which is compatible with a mass spectrometric analysis, such as, ammonium sulfate.

Each individual fraction is applied onto a coordinate of the ion source of a mass spectrometer, and then each coordinate is examined for the presence of the chemical modifications, which are differentiated by their weight. In this variant, for reasons pertaining to equipment, it is preferred to use a MALDI-TOF which has a very large ion source, making it possible to allow a very large number of different coordinates in short succession.

Additional variants of the method can be obtained because of the fact that the described method, in very general terms, generates all the measurement points in two dimensions, a necessity in the elaboration of numbers of measurement points, as described here. On DNA chips, these two dimensions are arranged spatially, as in the described variant of the analysis of individual "subreactions" on the ion source of a MALDI-TOF. In the capillary electrophoretic variant, the two dimensions are achieved by consecutive connection of two separation methods that separate by different criteria. Several additional variants of such a method exist, which, because they correspond to the overall concept according to the invention, should fall under the protection. For the measurement to be performed at a very large number of points in the context of the method according to the invention, it is not absolutely necessary to know for each measurement point what its origin is. For many applications of the method it is sufficient to correlate an enormous amount of abstract data with phenotypic properties of cells. As a result, there is a considerably larger spectrum of possible analytical methods. As a rule, however, a capillary electrophoresis is necessary in all the variants, in which the hybridization result that has occurred is detected by indirect means (the result itself being a dimension of analysis).

4.5 Analysis of the Generic Data

The main claims relate to the method, in general, for the preparation of complex methylation fingerprints, and for the correlation, by means of an evaluation algorithm, with phenotypic characteristics of the examined cells. The patent protection should, however, also apply to all the methods which are suitable for the generation of methylation data with the goal of carrying out an evaluation, according to the invention, of these data, because the generation and use of the data in combination is the factor which in fact reaches the level of inventive activity.

At the end of all of the above-described process steps, an enormous number of measurement points is available. Three different types of values can be produced. Pure plus-minus signals for positions, which arc present either in methylated or tnmethylated form on all analyzed chromosomes, probably do not constitute the largest group of the detectable positions that can be methylated. A very large number of positions will generate such signals, which must be described with the above-mentioned methods.

In principle, the analysis of pure plus-minus signals is considerably simpler. The analysis strategy should look as follows. From many different DNA samples of known origin (for example, from antibody-labeled cells of the same phenotype, isolated by immunofluorescence), data are generated in a large number of tests, and their reproducibility is tested. Positions which do not yield reproducible results are separated from all the others by logical means, because, in a first step, no evaluation is to be carried out to determine whether differences at individual positions are of biological significance. These test series are to be performed on cells of different types. The results of these test series should be a large, today still unknown, number of CpG dinucleotides which, in comparison to any pair of cell types, produce a reproducible difference in their methylation state. Not all positions that are different in the direct comparison of two cell types will be informative in all such comparisons regarding their difference. If one now analyzes all the positions which are distinguishable in at least one cell type comparison, then a characteristic pattern can be established for each tested cell type. In this manner, a DNA sample of unknown origin can be assigned to a cell type. These patterns are not necessarily constant in all the tested positions. At this time, one cannot evaluate (the method according to the invention in fact first provides a foundation for such an evaluation) to what extent the methylation pattern of a cell type from one individual sample deviates from the characteristic mean.

In the ideal case, the pattern generated per cell type and individual is so constant that such a tissue can be identified without large expenditure. A predetermined matrix with the defined characteristic signal coordinates can then be used directly for the assignment of the sample to a cell type. In the most complicated case, it is not an individual definable pattern of signals which is characteristic for a cell type, rather, there are many such patterns, which are fundamentally characteristic, but can, apparently not be identified as such. Indeed, and this can be derived from the state of the art in the methylation analysis, it is possible that patterns which appear to be very different contain very similar functions. However, at this time no statement can be made regarding the degree of this difficulty, because the method of the invention in fact first makes available the possibility of evaluating such a situation. Thus, what may be the case is that, using conventional methods, so to speak "by visual inspection," a sample cannot be assigned to an origin. In this case, the method proposed comprises the possibility of "training" a "neural network" (NN) with the data determined in the test series. In practice, this looks as follows: A very large number of test series is run with cell DNA samples, and fed into the input level of the NN. At the same time, with the methylation data of the sample., the NN is supplied information on the origin of the samples. A neural network can then, after a sufficient number of tests, learn, so to speak, what patterns belong to what cell types. In this manner, such extremely complex and apparently nontransparent patterns can be classified, which, to human understanding and conventional algorithms, appear to be completely chaotic.

However, as stated, it cannot yet be predicted how complex and apparently chaotic the generated patterns will be in appearance. Every case between the described ones is possible. Therefore, every method which uses the assignment of complex methylation patterns to cell types of known origin in test series, in order to be able to classify the used cell types of unknown origin, is an object of the present invention.

The analysis of the data will certainly become more complicated in the analysis of cells of aberrant origin. The purpose of the proposed method is to permit the classification of unknown disease cell types. With the methylation data of the examined samples, phenotypic parameters of the examined cells must therefore be made available during the test series to the NN and/or other evaluation system, and, in this context, it is at first not clear at all which of these phenotypic data need be correlated at all with the methylation pattern and which produce reasonable data within the context of such a correlation. In such cases, the difficulties are increased which originate from the apparently chaotic, although in principle classifiable, data quantities. It may be that in the case of degenerated cells, different epigenotypic states lead to similar phenotypic characteristics. Such situations are recognized particularly well by NNs, and they can then lead to the definition of new, precisely differentiated phenotypes, which is one of the main purposes of the proposed method. It is therefore desirable to explicitly include in the patent protection the use of the different types of neural networks in the analysis of methylation data for the correlation of methylation patterns with phenotypic data. However, the simpler situations can also fulfill the essence of the invention, and they should therefore not be excluded from patent protection.

What is claimed is:

1. Method for the characterization, classification and differentiation of tissues and cell types, for the prediction of the behavior of tissues and groups of cells, and for the identification of genes with modified expression, characterized in that in genomic DNA, which has been obtained from any tissue sample, and which may have been treated, subjected to shearing, or cleaved by means of a restriction endonuclease, the base cytosine, but not 5-methylcytosine, is converted by treatment with a bisulfite solution into uracil, fractions of the so-treated genomic DNA are amplified by the use of either very short or degenerated oligonucleotides or, in the case of cleaved or sheared genomic DNA, oligonucleotides which are complementary to adaptor oligonucleotides that have been ligated to the end of the cleaved or sheared genomic DNA before the bisulfite treatment, overall, the quantity of the remaining cytosine on a strand from the amplified fractions that contains more guanine than cytosine and/or the quantity of guanines on a strand from the amplified fractions that contains more cytosine than guanine are detected by a hybridization or polymerase reaction, which is such that the data generated in such an analysis and automatically applied to a processing algorithm make it possible to draw conclusions regarding the phenotype of the analyzed cell material.

2. Method according to claim 1, characterized in that the data obtained from this analysis of several or many such tests on DNA samples from phenotypically identical or similar cells or tissue are correlated in a training phase using a neural network or other evaluation algorithm with the phenotype of the cells, whose DNA was examined, the data included in this training phase in an evaluation pattern revealed by applying said evaluation algorithm on the connection between the phenotype and the methylation state are used for deriving, by the generation of a methylation state of a DNA sample of unknown origin, the phenotype of the cells whose DNA was examined, or the data included in this training phase in an evaluation pattern revealed by applying said evaluation algorithm on the methylation state of the DNA of a known cell type are used for identifying cytosine positions which differ in the examined DNA from the methylation state determined in the training phase.

3. Method according to claim 1, characterized in that the DNA is cleaved prior to the treatment with bisulfite and restriction endonucleases that contain cytosine in the 5'-CpG-3' context in their recognition sequence, and in that the DNA is cleaved only at those recognition sequences, in which cytosine, in the 5'-CpG-3' context, is in the unmethylated form in the 5' position.

4. Method according to claim 1, characterized in that, before the genomic DNA is modified with a bisulfite solution, this genomic DNA is cleaved with a restriction endonuclease, the resulting ends are provided, by means of a ligation reaction, with known, short and double-stranded DNA sequences, also called adaptors, oligonucleotides, which are complementary to the adaptors that have been treated with bisulfite, are used for the purpose of amplifying all the DNA fragments or subpopulations so generated from the totality of all the fragments produced in this manner after a treatment with bisulfite.

5. Method according to claim 1, characterized in that the reaction of a genomic DNA sample with a bisulfite solution, for the purpose of converting cytosines to uracils while simultaneously obtaining methylcytosine, takes place under cyclic variation of the reaction temperature between 0° C. and 100° C.

6. Method according to claim 1, characterized in that the DNA sample, before the treatment with bisulfite, is transferred into a heatable porous capillary, which is only permeable to small molecules, in which the following reaction steps of the bisulfite treatment can be carried out by adding and removing reagents by dialysis.

7. Method according to claim 1, characterized in that the DNA sample, before the treatment with bisulfite, is transferred into a heatable capillary that is impermeable to small molecules, in which the following reaction steps of the bisulfite treatment can be carried out by the addition and removal of the reagents by supplying reagents through connected capillaries.

8. Method according to claim 1, characterized in that the polymerase reactions which follow the bisulfite treatment are carried out in the same capillary as the bisulfite treatment, or in a capillary connected to this capillary, or in a container connected to this capillary.

9. Method according to claim 1, characterized in that, in a capillary in which the polymerase reactions are carried out with a DNA sample treated with bisulfite, a separation by length of the fragment population produced is also carried out.

10. Method according to claim 1, characterized in that a treated DNA is separated from the bisulfite by precipitation of the bisulfite.

11. Method according to claim 1, characterized in that, for the amplification of the genomic DNA samples treated with bisulfite, oligonucleotides of two classes are combined, where the oligonucleotides of one class do not contain the base cytosine or analogs thereof, except in the 5'-CpG-3' context, or to only a very small degree, or only in regions of the oligonucleotides that are not essential for the amplification, and where the oligonucleotides of the other class do not contain the base guanine or analogs thereof, except in the 5'-CpG-3' context, or to only a very small degree, or only regions of the oligonucleotides which are not essential for amplification, and where the two classes of oligonucleotides either
  a) are so short that, in an amplification where each contains only one representative of the two classes, more than 100 different fragments are amplified, or
  b) contain so many degenerated positions that in an amplification with only one representative of each of the two classes, more than 100 different fragments are amplified, or
  c) are used in such great numbers that, in an amplification, more than 100 different fragments are amplified.

12. Method according to claim 4, characterized in that the treated and amplified DNA are mixed in separate preparations for the purpose of polymerase reactions, with different oligonucleotides in each reaction which are complementary at their 5' termini to the adaptors or generally complementary for the amplification of the oligonucleotides treated with bisulfite, and which are different at their 3' termini in each reaction, and whose variable 3' termini start downstream of the known adaptor sequence or oligonucleotide sequence, and their variable 3' termini extend beyond the known adaptor sequence by 2–12 nucleotides into the unknown template DNA sequence.

13. Method according to claim 12, characterized in that such reactions, in which a polymerase reaction with oligonucleotides is started, which oligonucleotides are complementary to DNA treated with bisulfite, contain, in addition to the three nucleotides dATP, dTTP and dCTP, or analogs of these three nucleotides,
a nucleotide analog that is complementary to the base cytosine and which, after incorporation by the polymerase, blocks any further elongation of the strand, or
no nucleotide or nucleotide analog that is complementary to the base cytosine.

14. Method according to claim 12, characterized in that such reactions, in which a polymerase reaction with oligonucleotides is started, which oligonucleotides are complementary to DNA treated with bisulfite, contain, in addition to the three nucleotides dATP, dTTP, and dGTP, or analogs thereof, three nucleotides,
a nucleotide analog that is complementary to the base guanine and which, after incorporation by the polymerase, blocks any further elongation of the strand, or
no nucleotide or nucleotide analog that is complementary to the base guanine.

15. Method according to claim 12, characterized in that the termination of a polymerase reaction, at the positions which earlier contained methylcytosine in the DNA sample, takes place by such terminators, which themselves have been modified in such a manner that they allow the detection of the specifically terminated polymerase reaction products.

16. Method according to claim 1, characterized in that the different fragment mixtures of the individual reaction preparations are applied to individual points of the ion source of a MALDI-TOF or another mass spectrometer, and the fragment composition of the individual reactions is determined by determining the weight of all the DNA fragments.

17. Method according to claim 1, characterized in that the different fragment mixtures of the individual reaction preparations are applied to individual lanes in gel electrophoresis, and the fragment compositions of the individual reactions are determined by determining the lengths of all the DNA fragments.

18. Method according to claim 4, characterized in that the oligonucleotides which are complementary at their 5' termini to the adaptors or generally complementary for the amplification of the oligonucleotides treated with bisulfite, and which are different at their 3' termini in each reaction, and whose variable 3' termini start downstream of the known adaptor sequence or oligonucleotide sequence, and their variable 3' termini extend beyond the known adaptor sequence by 2–12 nucleotides into the unknown template DNA sequence, by means of which polymerase reactions are started, are each coupled with an oligonucleotide having a different sequence and different chemical labels, in that their chemical and/or physical properties allow the detection and differentiation of the different labels by standard chromatographic or mass spectrometric procedures.

19. Method according to claim 18, characterized in that the fragment fraction, prepared in the first amplification step, of the DNA to be examined, which has been treated with bisulfite, is mixed simultaneously with two or more chemically differently labeled oligonucleotides, these oligonucleotides are used in a reaction preparation as primers for a polymerase reaction, the resulting complex mixture of fragments is subjected in a first analytical step to an electrophoretic separation by length, and the individual length fractions of the fragment mixtures resulting from the electrophoresis are subjected to a chromatographic or mass spectrometric analysis, which detects, in each length fraction, the presence or absence of the chemical labels that characterize the oligonucleotides.

20. Method according to claim 1, characterized in that, onto a surface, oligonucleotides are applied which either do not contain the base cytosine or analogs thereof, or only in the 5'-CpG-3' context, or only in regions which are not essential for hybridization with sample DNA, or which do not contain the base guanine, or contain it only in the 5'-CpG-3' context, or in regions which are not essential for hybridization with sample DNA.

21. Method according to claim 20, characterized in that the DNA sample, which has been treated with bisulfite and amplified according to claim 4 or claim 11, is hybridized with oligonucleotides that are fixed to a surface, which oligonucleotides have been fixed to this surface so that it is known, for each point of the surface, which oligonucleotide sequence is located precisely at that point, a hybridization of the amplified sample DNA with the fixed oligonucleotides occurs, or persists only after appropriate washing steps, if oligonucleotides and the sample DNA are completely complementary in the regions that are essential for a hybridization.

22. Kit for use in characterizing, classifying and differentiating tissues and cell types, for use in predicting the behavior of tissues and groups of cells, and for use in identifying genes with modified expression, said kit comprising a first set of oligonucleotides for use in amplifying bisulfite-treated DNA and a second set of oligonucleotides that are fixed to a matrix in a pre-determined manner so that it is known for each point on the matrix which oligonucleotide is located at said point, said first set of oligonucleotides being very short or degenerated oligonucleotides, being oligonucleotides which are complementary to adaptor oligonucleotides that have been ligated to the end of DNA before bisulfite treatment, or being two classes of oligonucleotides that are combined, where the oligonucleotides of one such class do not contain the base cytosine or analogs thereof, except in the 5'-CpG-3' context, or to only a very small degree, or only in regions of the oligonucleotides that are not essential for amplification, and where the oligonucleotides of the other such class do not contain the base guanine or analogs thereof, except in the 5'-CpG-3' context, or to only a very small degree, or only regions of the oligonucleotides which are not essential for amplification.

23. Method according to claim 11, characterized in that the treated and amplified DNA are mixed in separate preparations for the purpose of polymerase reactions, with different oligonucleotides in each reaction which are complementary at their 5' termini to an adaptor sequence or complementary for the amplification of the oligonucleotides treated with bisulfite, and which are different at their 3' termini in each reaction, and whose variable 3' termini start downstream of the adaptor sequence or oligonucleotide sequence, and their variable 3' termini extend beyond the adaptor sequence by 2–12 nucleotides into an unknown template DNA sequence.

24. Method according to claim 11, characterized in that the oligonucleotides, which are complementary at their 5' termini to an adaptor sequence or complementary for the amplification of the oligonucleotides treated with bisulfite, and which are different at their 3' termini in each reaction, and whose variable 3' termini start downstream of the adaptor sequence or oligonucleotide sequence, and their variable 3' termini extend beyond the adaptor sequence by 2–12 nucleotides into an known template DNA sequence, by means of which polymerase reactions are started, arc each coupled with an oligonucleotide having a different sequence and different chemical labels, in that their chemical and/or physical properties allow the detection and differentiation of the different labels by standard chromatographic or mass spectrometric procedures.

* * * * *